United States Patent [19]

Earl et al.

[11] Patent Number: 4,504,666

[45] Date of Patent: Mar. 12, 1985

[54] HIGH YIELD PREPARATION OF AROMATIC AMINE OXIDES

[75] Inventors: Gary W. Earl, Bexley; Howard M. Hickman, Worthington, both of Ohio

[73] Assignee: Sherex Chemical Company, Inc., Dublin, Ohio

[21] Appl. No.: 385,000

[22] Filed: Jun. 4, 1982

[30] Foreign Application Priority Data

Jul. 3, 1981 [JP] Japan ............................... 56-103210
Aug. 18, 1981 [JP] Japan ............................... 56-93011
Oct. 24, 1981 [JP] Japan ............................... 56-169427

[51] Int. Cl.$^3$ .................. C07D 213/61; C07D 251/00; C07D 239/02; C07D 241/46
[52] U.S. Cl. .................................... 546/345; 544/349; 544/358; 544/336; 544/242; 544/224; 544/235; 544/347; 544/264; 544/253; 546/1; 546/348; 546/153; 546/112; 546/141; 564/298
[58] Field of Search ............... 546/345, 347, 153, 112, 546/141, 153, 290; 544/336, 242, 224, 215, 235, 347, 264; 564/298

[56] References Cited

U.S. PATENT DOCUMENTS 2,745,826  5/1956  Semenoff et al. .................. 546/345

OTHER PUBLICATIONS

Shaw, et al., J. Am. Chem. Soc., 72, 4362, (1950).
Finger, et al., J. Org. Chem., 24, 2674, (1959).
Ochiai, J. Org. Chem., 18, 534, (1953).
Noller, Textbook of Organic Chemistry, p. 165, W. B. Saunders Co., Philadelphia, 1966, 3rd Ed.

*Primary Examiner*—Henry R. Jiles
*Assistant Examiner*—Robert C. Whittenbaugh
*Attorney, Agent, or Firm*—Mueller and Smith

[57] ABSTRACT

Disclosed is an improvement in process for oxidizing an aromatic amine to form an aromatic amine oxide wherein a reaction mixture of the aromatic amine and a peracid is formed and maintained under non-aqueous conditions at a temperature and for a time adequate until substantially all of the aromatic amine is formed into said aromatic amine oxide. The provision for eliminating water from the reaction mixture leads to near quantitative yields of aromatic amine oxide.

23 Claims, No Drawings

HIGH YIELD PREPARATION OF AROMATIC AMINE OXIDES

BACKGROUND OF THE INVENTION

The present invention relates to the preparation of amine oxides and more particularly to a method for preparing aromatic amine oxides rapidly in high yield.

The preparation of aliphatic amine oxides from tertiary amines is a known process. The preferred oxidizing agent therefor is a peroxidizing agent, such as hydrogen peroxide, typically provided in aqueous form, though peracids additionally may be used as the oxidizing agent. Relatively mild oxidation conditions for such process typically comprehends temperatures of about 60°–80° C. or thereabouts under sub-atmospheric, atmospheric, or super-atmospheric pressure. Reaction times can range from as short as a few hours on up to 10–15 hours or more depending upon the oxidation conditions and particular reactants used.

Unfortunately, the preparation of aromatic amine oxides from aromatic amines is not so simple a procedure as is the preparation of aliphatic amine oxides. For example, hydrogen peroxide is too weak of an oxidizing agent to be effective. Thus, the use of peracids is dictated. Shaw et al., J. Am. Chem. Soc., 72, 4362 (1950) oxidizes 2-bromopyridine with perbenzoic acid or peracetic acid to form the corresponding aromatic amine oxide. Reported reaction times amount to several days with 60–70 percent yields resulting. Finger and Starr, J. Org. Chem., 24, 2674 (1959) show the preparation of 2-chloropyridine-N-oxide by reacting 2-chloropyridine with glacial acetic acid and 40 percent peracetic acid. An 80 percent yield is reported after about 22 hours reaction time.

Semenoff, U.S. Pat. No. 2,745,826, oxidizes 2-bromopyridine with 40 percent peracetic acid to obtain a 71 percent yield of the desired amine oxide product in about 4 hours. Ochiai, J. Org. Chem., 18, 534 (1953) also shows the use of glacial acetic acid and 35 percent aqueous hydrogen peroxide to form pyridine-N-oxide in about 96 percent yield after 12 hours reaction. Quinoline-N-oxide was similarly prepared using 29 percent aqueous hydrogen peroxide to obtain the desired product in about 92 percent yield after an unspecified reaction time.

Common in these prior proposals in the preparation of aromatic amine oxides only after extended reaction times and then generally to no more than about a 60–80 percent yield. Also, cumbersome and time consuming purification of the resulting products are reported. While such yields may appear to be satisfactory at first glance, it must be remembered that the aromatic amine reactants, eg. 2-chloropyridine, often range in price to several dollars per pound. The high cost of such reactants necessarily dictates that a very efficient commercial process be employed in order to provide a commercially, economically viable process. Moreover, a simple method for recovery of the desired product also is necessary. Even if these objectives were accomplished, economics of the marketplace also dictate that reaction times be reduced substantially in order to make the process more commercially viable and attractive. The present invention provides an answer to the commercial need for the preparation of aromatic amine oxides rapidly, at moderate reaction conditions, and in essentially stoichiometric yields.

BROAD STATEMENT OF THE INVENTION

The present invention is an improvement in process for oxidizing an aromatic amine to form an aromatic oxide. Such improvement comprises reacting the aromatic amine with a peracid while maintaining non-aqueous conditions until substantially all of said aromatic amine is formed into said aromatic amine oxide. Desirably, the peracid is formed in situ in the reaction mixture which also contains a water excluder or substance which reacts with and/or absorbs or adsorbs water for maintaining said anhydrous conditions. Reaction temperatures approximate those encountered in the formation of aliphatic amine oxides, eg. 60°–80° C. Reaction times experienced in the process often range on up to an hour or more with essentially stoichiometric yields of the desired aromatic amine oxide being formed.

Advantages of the present invention include the high yields of product which means that no provision need be made in the process for recovering and recycling unreacted starting material. Additionally, the relatively mild reaction conditions and quick reaction times further contribute to the ease of implementing the process commercially as well as enhance its economic viability. Further, the process of the present invention has been designed to be quite safe even in larg-volume reaction mixtures which necessarily must be used in commercial scale practice of the present invention. These and other advantages will be readily apparent to those skilled in the art based upon the disclosure contained herein.

DETAILED DESCRIPTION OF THE INVENTION

A wide variety of aromatic amines can be subjected to the process of the present invention for rapidly preparing aromtic amine oxides in high yield. Pyridine and substitute pyridines, for example, find wide use in the process of the present invention because a variety of herbicides and pharmaceutical compounds can be made from various substituted pyridine amine oxides. Additional aromatic amines include, for example, pyrizine, pyrimidine, pyridazine, indolizine, isoquinoline, quinoline, pyridine, picoline, quinaldine, phthalazine, quinoxaline, cinnoline, phenazine, and the like, and even mixtures thereof. Such aromatic amines may be substituted with a variety of substituents and still find use in the process of the present invention. Such substituents include, for example, halogen, nitrile, hydroxyl, ether alkyl, amide, carboxylic acid and alkyl esters thereof, and the like. So long as such substituents do not react with the reactants under the conditions used, such substituents will not adversely interfere with the formation of the amine oxide.

Most commercially available peracids are supplied in aqueous form. While such aqueous peracids may be used in the process of the present invention, provision for addition of a water-getter or excluder, i.e. a compound which effectively eliminates or excludes water as a participant in the reaction mixture, also is made. Alternatively, the aqueous peracid can be pre-treated prior to its addition to the reaction mixture wherein such treatment effectively removes or eliminates water therefrom. Such pre-treatment for water elimination from the aqueous peracid, though, tends to add additional costs to the process which may not be justified in light of the ability to design the process to operate effectively and efficiently with aqueous peracids. For both embodiments, the importance of maintaining "non-aqueous conditions" is important for obtaining the high yields in short reaction times under relatively mild oxidation conditions. By "non-aqueous conditions" is meant that conditions are established and maintained during the process so that water entering the reaction mixture or water of reaction is effectively eliminated as a reactant or participant during the reaction. Desirably, the peracids used in the process of the present invention are organic peracids and peracetic acid is preferred. Additional organic peracids include performic acid, perbenzoic acid, and the like. Stronger inorganic peracids also may be used in the process of the present invention, though their removal at later stages may be more difficult. The proportion of peracid used should be at least stoichiometric and preferably excesses of between about 1.2 and 1.5 times stoichiometric are used. Desirably, aqueous peracids of high peracid concentration are used in order to minimize entrance of water into the process.

As noted above, peracetic acid is preferred for use in the process of the present invention and such peracetic acid, or other peracid of choice, may be in aqueous form. Under this preferred embodiment of the present invention, the reaction mixture can be formed with acetic anhydride which functions as a solvent, as a reactant for elimination of water, and for the in situ formation of peracetic acid wherein aqueous hydrogen peroxide is added to a reaction mixture of the aromatic amine, acetic anhydride, and acid catalyst which promotes the in situ formation of peracetic acid. Note that a room temperature, the aromatic amines tend to be quite stable and are not oxidized even in the presence of the peracid, but at relatively mild reaction temperatures (eg. 60°-80° C.) the oxidation reaction is facile. Other methods for excluding water as a participant or reactant during the oxidation reaction include, for example, the use of molecular sieves, though separation of the sieves and later regeneration thereof is required. Additional water-getters include, for example, sodium sulfate, magnesium sulfate, calcium chloride, and like conventional water-getters. Again, though, an unwanted ingredient would be interjected into the system by use of such compounds. Yet another method for achieving the elimination of water is to use a solvent which forms an azeotrope with water which azeotrope can be distilled from the reaction mixture under the reaction conditions maintained. Traditional azeotroping solvents include, for example, benzene, toluene, and the like. The use of such aromatic solvents, though, is not preferred for minimizing costs of the process as well as reducing possible exposure to hazardous substances. Accordingly, the use of acetic anhydride of like anhydride solvents in proportions ranging up to about 3-5 times stoichiometric (based on the water entering the reaction mixture including water of reaction) distinctly is preferred for practicing the process of the present invention.

Since essentially pure aromatic amine oxide often is required for further processing, the use of solvents in the reaction mixture should be miminized. As noted above, when the in situ formation of the peracid, eg. peracetic acid, is practiced, the addition of an acid catalyst such as sulfuric acid or acidic (cationic) resin promotes the peracetic acid formation in the reaction mixture. No additional catalyst or other reactants normally are recommended in order to simplify subsequent processing of the product aromatic amine oxide. The reaction mixture typically is held at a temperature ranging from about 60°-80° C. for about one hour in order for the desired aromatic amine oxide to be formed. Generally, near quantitative or stoichiometric yields of the aromatic oxide are experienced according to the fundamental precept of the present invention which involves the maintaining of effective anhydrous or non-aqueous conditions during the oxidation process.

Some concern is known when handling the reagents preferred for use in the present invention, particularly when large volume reactions are involved. Thus, it is known that hydrogen peroxide forms potentially detonatable mixtures with organic material in well defined hydrogen peroxide ranges, eg. generally when the hydrogen peroxide represents about one-third by volume of the final mixture. From a practical standpoint, such high hydrogen peroxide concentrations are far in excess of that normally encountered in oxidation reactions. Metered addition of hydrogen peroxide to the reaction mixture in an effective way of ensuring that low concentrations of the hydrogen peroxide are present and is an effective means in avoiding impact-sensitive mixtures. Further, such metered addition of hydrogen peroxide to the reaction mixture typically means that much of the hydrogen peroxide is reacted prior to subsequent aliquot additions. Finally, the aromatic amine oxide product or products subsequently made are not recovered from the reaction mixture by distillation unless residual hydrogen peroxide or peracetic acid has been destroyed. Such precaution additionally is implemented easily in the commercial design of the present invention. Further, reliable analytical methods have been developed which ensure the continued monitoring of the reaction mixture to avoid potential hazardous situations. Such analytical methods will be further detailed in the examples which follow.

As noted above, the aromatic amine oxides find wide use as intermediates in the preparation of pharmaceuticals, herbicides, and like uses. For example, in the preparation of 2-chloropyridine-N-oxide, such compound can be readily converted to sodium omadine by well known techniques. The high yield and rapid preparation of such aromatic amine oxide has advantages in the omadine formation in that the high yields contribute to an economically viable process and the overall process can be conducted as a one-pot reaction through to the omadine product. Moreover, the product omadine is isolated as a low-colored product. While several methods for preparing sodium omadine are shown in the art (eg. U.S. Pat. No. 2,745,826), for best color stability, the pyridine oxide formed according to the process of the present invention is reacted with sodium sulfide which has been previously dissolved in a minimum of water. This rection mixture is heated to about 90° C. during which the metered addition of sodium sulfide is effected. The reaction mixture then provides a product which is the sodium salt of 2-mercaptopyridine-N-oxide. This aqueous system contains excess sodium sulfide and sodium acetate from a neutralization step also.

The omadine hydrochloride product can be isolated simply by acidifying the reaction mixture, eg. with concentrated hydrochloric acid, and the excess sodium sulfide liberated as hydrogen sulfide readily by a nitrogen sparge. The product 2-mercaptopyridine-N-oxide-HCl will crystallize on cooling. Filtration and drying results in the one-pot production of the omadine product in isolated yields on up to 90 percent.

The following examples show in detail how the present invention can be practiced but it should not be construed as limiting. In this application, all units are in the metric system and all percentages and proportions are by weight, unless otherwise expressly indicated.

IN THE EXAMPLES

The analytical method used to follow the progress of the oxidation reaction involved a gas chromatographic (GC) assay of the rate of disappearance of reactants (water and 2-chloropyridine). The column is a 1.22 m×3.175 mm (4'×⅛") Dexil 300 (3%) on Varaport 30 (90/100) using a 60°–180° program at 10° C./min. This method is quick and quantitative when run against an internal standard. Nuclear Magnetic Resonance (NMR) analysis was used to determine the appearance of product oxide and disappearance of reactants.

EXAMPLE 1

The oxidation reaction was conducted in a three-neck, round-bottom flask heated with an oil bath and kept under an inert atmosphere. The reaction mixture was magnetically stirred. Into the flask was charged 30 g of 2-chloropyridine (0.26 mole), 85.2 g of acetic anhydride (0.83 mole), and 6 g of resin acid catalyst. (The DOWEX acid catalyst was washed with glacial acetic acid containing 5% HCl then washed with diethyl ether, followed by air drying in order to ensure the acid form of the solid catalyst.) The reaction mixture was heated to 65°–70° as 30 g of 50% aqueous hydrogen peroxide (0.45 m) was metered in over a 1 hour time period. The reaction mixture was held at 70° C. for 2 hours more.

G.C. analysis showed only 2.3% of the initial charge of 2-chloropyridine had not reacted. A KI test showed no unreacted hydrogen peroxide, so the excess acetic acid solvent was stripped from the reaction mixture at 50° C. mm Hg. NMR structural analysis showed the residue to be the acetic acid salt of 2-chloropyridine-N-oxide (94% yield). Additional runs conducted in accordance with this example using 0.26 moles of 2-chloropyridine have resulted in oxide yields of 95%, 95%, and 99%.

EXAMPLE 2

The apparatus described in Example 1 was charged with 20.5 g of reagent grade pyridine (0.26 m, 99.8% concentration), 85 g of acetic anhydride (0.833 m), and 0.5 ml of concentrated $H_2SO_4$. The reaction mixture was heated to 60° C. as 30 g of 50% aqueous $H_2O_2$ (0.44 m) was added dropwise over a 1 hour time period. The temperature of the reaction mixture was maintained below 70° C. by occasional use of an ice bath. After 4 hours reaction time, the KI test showed no unreacted $H_2O_2$. Acetic acid and acetic anhydride were removed by evaporation to leave product pyridine-N-oxide ($C^{13}$ NMR showed no unreacted pyridine). A small amount of a contaminant, perhaps 2-acetoxypyridine, was noted. A yield of 92% product oxide was isolated.

EXAMPLE 3

The apparatus described in Example 1 was charged with 23.5 g of 2-picoline (b.p. 128°–129° C., $N_D^{20} = 1.5000$, Aldrich Chemical Company, 0.25 m) in 75 g of acetic anhydride (0.74 m). After adding 0.5 ml of concentrated $H_2SO_4$ and heating the reaction mixture to 65° C., 28.9 g of 50% aqueous $H_2O_2$ (0.43 m) was added dropwise over a 1.5 hour time period. The reaction mixture then was maintained at 65°–70° C. for 8 hours. $C^{13}$ NMR showed that all of the 2-picoline had been consumed. The same analysis confirmed the product 2-methyl-pyridine-N-oxide (96% yield).

EXAMPLE 4

To the apparatus of Example 1 was added 20 g of quinaldine (0.14 m of 2-methyl quinoline, b.p. 248° C., $N_D^{20}$ 1.6108, Aldrich Chemical Company) in 85 g of acetic anhydride (0.84 m). After 0.5 ml $H_2SO_4$ was added and the reaction mixture heated to 65° C., 13.3 g of 50% aqueous $H_2O_2$ (0.20 m) was added dropwise to the heated reaction mixture. The initial exotherm was controlled by an ice bath and the reaction temperature was kept at 70° C. for 6 hours. The $C^{13}$ NMR showed that all of the quinaldine had been oxidized and that the product had a spectrum consistent with quinaldine-N-oxide. The yield of oxide product was 98% with a small amount of a contaminant, perhaps 2-acetoxymethyl quinaldine being present. Another run conducted as described herein resulted in a 93% yield of oxide product from 0.25 moles of quinaldine feed.

EXAMPLE 5

To the apparatus of Example 1 was added 150 g of 2-chloropyridine (1.3 moles) and 426 g of acetic anhydride (4.18 moles). After 0.5 g of concentrated sulfuric acid was added and the reaction mixture heated to 75° C., 150 g of 50% aqueous $H_2O_2$ (2.2 moles) was added dropwise to the reaction mixture. The initial exotherm was controlled by an ice bath and the reaction mixture was maintained at 75° C. The KI test showed no residual hydrogen peroxide. The product reaction mixture was stripped at 50° C. and 50 mm Hg to yield 246 g of product 2-chloropyridine-N-oxide (88% yield).

We claim:

1. In a process for oxidizing an aromatic amine to form an aromatic amine oxide, the improvement characterized by:
forming a reaction mixture comprising said aromatic amine and a peracid comprising an organic peracid, an inorganic peracid, or mixtures thereof, and maintaining said reaction mixture under non-aqueous conditions at a temperature and for a time adequate until substantially all of said aromatic amine is formed into said aromatic amine oxide.

2. The process of claim 1 wherein said reaction mixture is formed from said aromatic amine and an anhydrous peracid.

3. The process of claim 2 wherein said peracid is formed in situ in said reaction mixture from its corresponding acid and aqueous hydrogen peroxide, said reaction mixture also containing a water-excluder which excludes water as a participant in the reaction mixture.

4. The method of claim 3 wherein an acid catalyst for said in situ peracid formation is included in said reaction mixture.

5. The method of claim 2 or 3 wherein said peracid is selected from the group consisting of peracetic acid, performic acid, perbenzoic acid, and mixtures thereof.

6. The method of claim 3 wherein said in situ formed peracid is peracetic acid which is formed from acetic anhydride and aqueous hydrogen peroxide.

7. The process of claim 3 or 6 wherein said water excluder is acetic anhydride.

8. The process of claim 1 wherein the temperature for said reaction mixture ranges up to about 60°–80° C.

9. The process of claim 1 wherein said aromatic amine is selected from the group consisting of pyrazine, pyrimidine, pyradazine, triazine, indolizine, isoquinoline, quinoline, pyridine, picoline, quinaldine, benzodiazine, phenazine, purine, substituted derivatives thereof, and mixtures thereof.

10. The process of claim 9 wherein said aromatic amine is 2-chloropyridine.

11. In a process of oxidizing an aromatic amine to form an aromatic amine oxide, the improvement characterized by:
(a) forming a mixture comprising said aromatic amine and an acid anhydride;
(b) adding an aqueous peroxide to said mixture and maintaining the resulting reaction mixture at a temperature and for a time adequate until substantially all of said aromatic amine is formed into said aromatic amine oxide, the proportion of said anhydride being adequate for forming a peracid in situ and for reacting with all water added to or formed in said reaction mixture.

12. The process of claim 11 wherein the proportion of said anhydride ranges from about 3 to 5 times the molar proportion of peroxide added to and of water added to or formed in said reaction mixture.

13. The process of claim 11 wherein said reaction temperature ranges from about 60° to 80° C.

14. The process of claim 11 wherein said acid anhydride is selected from the group consisting of acetic anhydride, formic anhydride, benzoic anhydride, and mixtures thereof.

15. The process of claim 14 wherein said anhydride is acetic anhydride.

16. The process of claim 11 or 15 wherein said aromatic amine is selected from the group consisting of pyrazine, pyrimidine, pyridazine, indolizine, isoquinoline, quinoline, pyridine, picoline, quinaldine, triazine, purine, benzodiazine, phenazine, substituted derivatives thereof, and mixtures thereof.

17. The process of claim 16 wherein said aromatic amine is 2-chloropyridine.

18. In a process for oxidizing an aromatic amine to form an aromatic amine oxide the improvement characterized by:
(a) forming a mixture of an aromatic amine and an acid anhydride;
(b) adding to said mixture formed in step (a) an anhydrous peracid and maintaining the resulting reaction mixture at a temperature and for a time adequate until substantially all of said aromatic amine is formed into said aromatic amine oxide, the proportion of acid anhydride in said reaction mixture being adequate to react with any water entering into or formed in said reaction mixture.

19. The process of claim 18 wherein said acid anhydride is selected from the group consisting of acetic anhydride, formic anhydride, benzoic anhydride, and mixtures thereof.

20. The process of claim 19 wherein said anhydride is acetic anhydride.

21. The process of claim 18 wherein the temperature for said reaction mixture ranges up to about 60°–80° C.

22. The process of claim 18 wherein said aromatic amine is selected from the group consisting of pyrazine, pyrimidine, pyridazine, indolizine, isoquinoline, quinoline, pyridine, picoline, quinaldine, phthalazine, quinoxaline, cinnoline, phenazine, substituted derivatives thereof, and mixtures thereof.

23. The process of claim 22 wherein said aromatic amine is 2-chloropyridine.

* * * * *

UNITED STATES PATENT AND TRADEMARK OFFICE
CERTIFICATE OF CORRECTION

PATENT NO. : 4,504,666
DATED : Mar. 12, 1985
INVENTOR(S) : Gary W. Earl and Howard M. Hickman It is certified that error appears in the above—identified patent and that said Letters Patent is hereby corrected as shown below:

In the section Foreign Application Priority Data, the following should be deleted:

"Foreign Application Priority Data

| Jul. 3, 1981 [JP] | Japan................56-103210 |
| Aug. 18, 1981 [JP] | Japan................56-93011 |
| Oct. 24, 1981 [JP] | Japan................56-169427" |

Column 4, line 41, "omadine" should read -- Omadine® --.

Signed and Sealed this

Twelfth Day of November 1985

[SEAL]

Attest:

Attesting Officer

DONALD J. QUIGG

Commissioner of Patents and Trademarks